United States Patent [19]
Widen et al.

[11] 3,969,824
[45] July 20, 1976

[54] SELF CLEANING DENTAL MIRROR

[76] Inventors: Randy Miles Widen, 1601 18th St. NW., Washington, D.C. 20009; Donald Simon, 1762 Spruce St., Berkeley, Calif. 94709

[22] Filed: Dec. 18, 1974

[21] Appl. No.: 534,136

[52] U.S. Cl. .................................... 32/69; 350/63
[51] Int. Cl.² .......................................... A61C 3/00
[58] Field of Search .................... 32/69; 128/21, 22; 350/63

[56] References Cited
UNITED STATES PATENTS

| | | | |
|---|---|---|---|
| 2,834,109 | 5/1958 | O'Hara | 32/69 |
| 2,907,110 | 10/1959 | O'Hara | 32/69 |
| 2,984,009 | 5/1961 | Codoni | 32/69 |
| 3,006,073 | 10/1961 | McCarter | 32/69 |
| 3,027,644 | 4/1962 | Piscitelli | 32/69 |
| 3,052,031 | 9/1962 | Piscitelli | 32/69 |

*Primary Examiner*—Robert Peshock
*Assistant Examiner*—Jack Q. Lever
*Attorney, Agent, or Firm*—Spencer & Kaye

[57] ABSTRACT

A self cleaning dental mirror apparatus utilizing the fluid dynamic properties of water and air to siphon the water across the reflective surface by air pressure through nozzle flanges surrounding a portion of the rim of the mirror surface, thus allowing the dentist free and continuous use of the dental mirror apparatus without interference from debris, mist and sprays normally produced in everyday dental operations. The apparatus is adaptable to standard dental consoles with means to regulate, measure and control all fluids separately or simultaneously and to provide a regulating means to control the amount of surface tension reducer operating through the water system.

16 Claims, 12 Drawing Figures

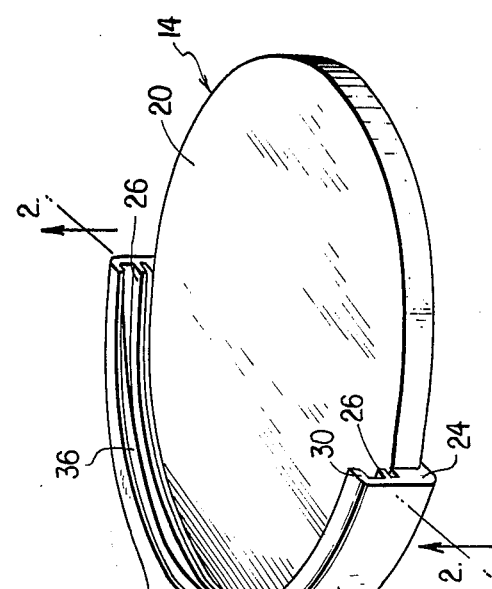
FIG. 2
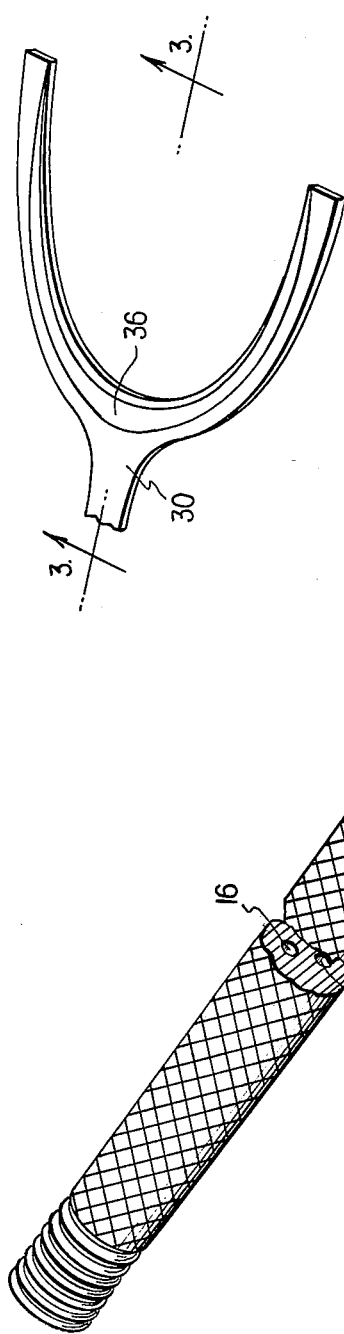
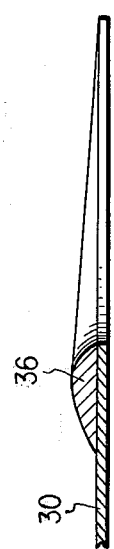
FIG. 3
FIG. 1

SELF CLEANING DENTAL MIRROR

BACKGROUND OF THE INVENTION

The present invention relates to dental instruments and more particularly to a self cleaning dental hand mirror. During use, the reflective surface of the dental hand mirror commonly used by dentists quickly becomes obscured from the dentist's high speed drill sprays, dental material and tooth debris, fog, mist, etc. This impaired reflective surface can lead to reduced workmanship in dental operations unless the mirror is constantly cleaned and/or a surface tension reducer constantly applied. It has therefore been customary for dentists to frequently remove these dental mirrors from the patients mouth to facilitate cleaning of the reflective surface and then to reposition the mirror in its original position, a process which is tedious, time consuming and costly. In addition to the time consuming and costly aspects of the present state of the dental mirror art there also arises a lack of concentration and pin point accuracy when the dentist is continuously interrupted to clean the mirror's surface. A few dentists have overcome this difficulty by eliminating the use of the dental hand mirror altogether. However this is often done by positioning the patient at an uncomfortable angle that will facilitate clear direct vision by the use of a special and more costly dental chair. However, many patients do not easily tolerate these uncomfortable positions. Additionally many dentists will crook or bend their necks and backs in an attempt to obtain direct vision, resulting in discomfort for the dentists.

Numerous attempts have been made to solve the problem of foggy, unclean dental mirrors and as early as 1906 a U.S. Pat. No. 838,648 was issued to Oliver T. Robinson, for a self cleaning dental mirror. Since then self cleaning dental mirrors have been proposed where air pressure is used to clean the reflective surface, or where water is used to wash the reflective surface. Each of these attempts, however, has proven unsatisfactory. Air pressure alone fails to prevent the formation of fog, mist, etc. from obscuring the mirror's surface. Likewise, when used alone, water either produces turbulent water patterns which distort the reflective surface beyond visability when supplied at a sufficiently high pressure to remove the high density debris which falls on the reflective surface during normal dental operations or, when supplied at a sufficiently low pressure so that distortion does not occur, does not wash the reflective surface clean of the high density debris. In order to attempt to overcome the various problems in using either air or water alone, devices have been patented that use water and air as an aspirating means. These devices, however, generally only attract the debris and mist to the reflective surface instead of away from it, and furthermore are susceptible to particles of debris clogging the aspirating vacuum inlets producing an uneven water flow and ripples across the mirror resulting in a distorted surface with unclear visibility.

Various other arrangements, including mechanical wipers, have even been tried without success. The most recent devices proposed use a combination air and water external mix nozzle, similar to a standard mouth wash spray device, to produce a spray across the surface of the mirror. Even though these devices remove most of the debris and mist, the turbulent interference patterns created by the spray makes these devices unacceptable because of poor visibility. Until the present invention, there has not been a practical workable self cleaning dental mirror device available to dentists.

SUMMARY OF THE INVENTION

It is an object of this invention to provide a dental hand mirror apparatus utilizing a combination of air and water flows that will produce a continuously clean and clear reflective surface.

A further object of this invention is to provide a dental hand mirror with a laminar flow of air specifically designed for minimal spray interaction with the cleasning water to uniformly and evenly move the water and/or a surface tension reducer in a fine film across the mirror's reflective surface.

A further object of this invention is to provide a self cleaning dental mirror that is easily and quickly taken apart and cleaned.

A unique feature of this invention is to provide a dental mirror with an air nozzle which produces a non-interference laminar air flow for siphoning the cleansing fluids across the mirror's surface and which provides a protective air curtain.

An important object of this invention is to provide a dental mirror with a water nozzle designed to present an even and complete distribution of water across the mirror's surface.

An important object of this invention is to provide a regulator control apparatus and fluid distribution unit which allows the dentist to operate the dental mirror cleansing device without cumbersome hand controls.

A further object of this invention is to provide a fluid mix reservoir system where material amounts of concentrated fluid are dispensed by valves so as to control the flow rate of the fluid in accordance with the water flow.

The above objects are basically achieved according to the present invention in that in a dental mirror having a disk-like mirror, an elongated handle, and means at one end of the handle for supporting the mirror, the handle is provided with a liquid conduit and a gas conduit which extend therethrough, a first nozzle means, which is disposed in the support means and is associated with said liquid conduit, dispenses a thin layer of a liquid onto the surface of the mirror, and a second nozzle means, which is disposed in the support means above the first nozzle means and is associated with the gas conduit, dispenses a thin layer of gas across and parallel to the surface of the mirror in a laminar flow above the layer of liquid to draw the layer of liquid across the surface of the mirror in a laminar flow.

The invention thus uses a liquid, e.g., water to clean the reflective mirror surface and a gas, e.g., air, to siphon the water in a thin laminar flow across the mirror surface making it possible to maintain the reflective surface in a clean unfogged state during the dental operation. By using a unique combination of separate air and water control systems and nozzles, air is dispensed through a nozzle surrounding one half of the rim or periphery of the mirror surface to effect siphoning or drawing of the water in a fine non-turbulent film smoothly across the mirror's reflective surface. The air stream in addition to siphoning the water creates a protective curtain of high pressure air preventing heavy debris or strong sprays from interfering with the reflective quality of the mirror surface. Any particles penetrating the air curtain are effectively washed off by the water flow.

BRIEF DESCRIPTION OF THE DRAWINGS

FIG. 1 is a perspective view of a preferred embodiment of a self cleaning dental mirror according to the invention.

FIG. 2 is a partial sectional view along the lines 2—2 of FIG. 1.

FIG. 3 is a cross-sectional view along the lines 3—3 of FIG. 2.

DESCRIPTION OF THE PREFERRED EMBODIMENTS

Figure 4:
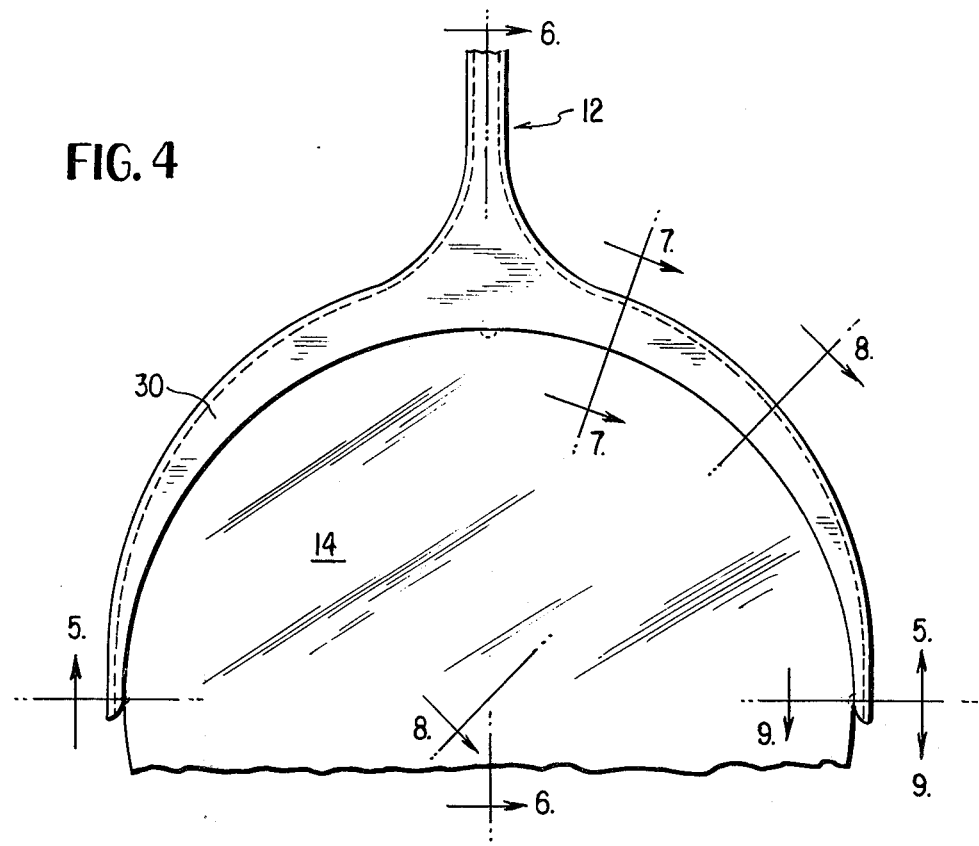
FIG. 4 is a partial plan view of a slightly modified embodiment of the dental mirror of FIG. 1.
Figure 5:
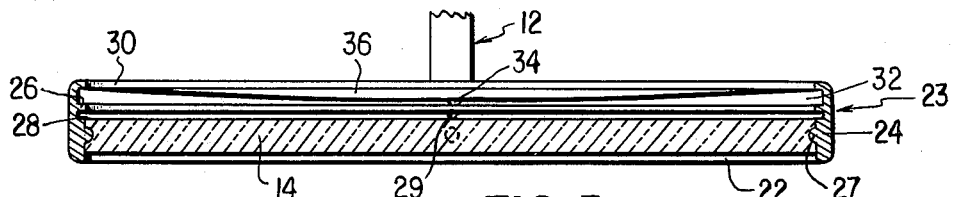
FIG. 5 is a cross-sectional view taken along the lines 5—5 of FIG. 4.

Referring to FIGS. 1 to 9, there is shown a dental mirror according to the invention having a hand grip or handle 10 with a support 12 for a reflective mirror 14 at one end thereof. The mirror 14 is the conventional circular type mirror presently used by dentists and if desired may be provided with means for removably fastening the mirror 14 to the support 12.

As best shown in FIG. 1, running through the handle or grip 10 are two conduits 16, 18 having a relatively small diameter, for example, 0.5 mm or less. The upper fluid conduit 16 serves to supply a gas, for example, air, and the lower fluid conduit 18 serves to supply a liquid, for example, water, to the reflective surface 20 of the mirror 14 via specially designed dispensing nozzles formed in the mirror support 12.

As shown in FIGS. 1 and 4, the support 12 for the mirror 14 includes an arcuate portion which extends around one half of the circumference or periphery of the mirror 14 and is symmetrical with respect to the handle 10. As shown in FIGS. 5 through 9, the arcuate portion of the support 12 includes a bottom plate 22 with an upwardly extending semi-circular rim 23 having a portion 24 which abuts the periphery of the mirror 14 and whose upper surfaces 25 is coplanar with the surface of the mirror 14. The bottom plate 22 and the semi-circular rim portion 24 provide the actual support for the mirror 14. The mirror 14 may be fixedly mounted in this rim portion 24, or if desired may be removably mounted therein, for example, by means of detents 27.

Figure 6:
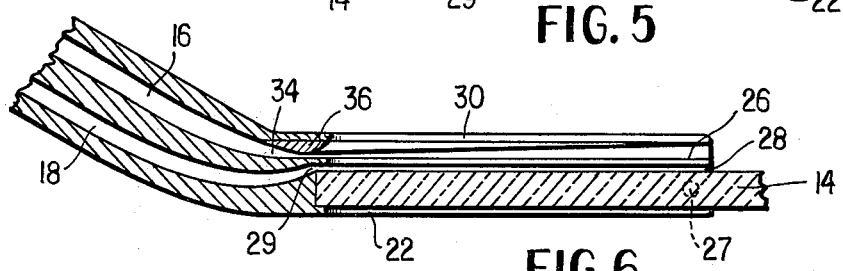
FIG. 6 is a longitudinal sectional view taken along the lines 6—6 of FIG. 4.
Figure 7:
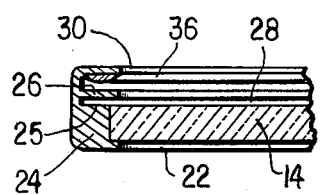
FIG. 7 is a partial cross sectional view taken along the lines 7—7 of FIG. 4.
Figure 8:
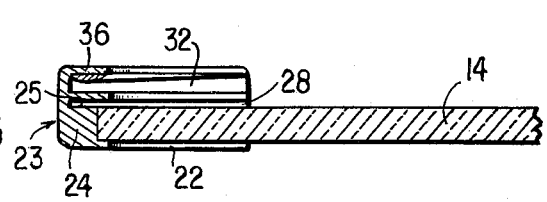
FIG. 8 is a partial cross-sectional view taken along the lines 8—8 of FIG. 4.
Figure 9:
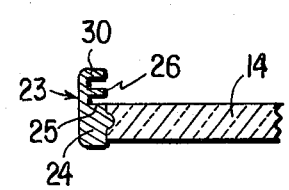
FIG. 9 is a partial cross-sectional view taken along the lines 9—9 of FIG. 4.

Attached to the rim 23 and extending above the surface 25 over a portion of the edge of the mirror 14, is a horizontally extending flange 26 which is parallel to the reflective surface 20 of the mirror 14 and extends along the entire length of the arcuate portion of the support 12. As shown in FIG. 6, the end 29 of the conduit 18 opens and is in communication with the space 28, between flange 26 and the mirror surface or surface 25 of the rim portion 24, which constitutes the dispensing nozzle for the water. According to the present invention, the spacing between the flange 26 and the underlying surface is sufficiently small so that a capillary action will result. Spacings in the order of 15 to 30,000ths of an inch have been found satisfactory for this purpose. Preferably as shown in FIG. 4 and as illustrated by the sectional views of FIGS. 7 to 9, the flange 26 is provided with a tapering width which narrows in a direction away from the handle 10.

In order to provide a dispensing nozzle for the air, a further horizontally extending flange or cover plate 30, whose outer surface area is coextensive with that of flange 26, is provided above and spaced from flange 26. The space 32 defined by the lower surface of the cover plate or flange 30 and the upper surface of the flange 26 is in communication with the orifice 34 of the conduit 16 constitutes the air dispensing nozzle. As indicated above, according to the invention the air dispensing nozzle is to provide a layer of air parallel to the surface of the mirror in a laminar flow. In order to achieve this result, an obstruction, e.g., a stationary vane is placed in the air dispensing nozzle 32 which has the effect of shaping the effective spacing for the air so that it is smallest and compressed immediately in front of the orifice 34 and effectively becomes wider and less compressed as it approaches the tips of the flanges 26 and 30 furthest from the orifice 34. Preferably, as shown in FIGS. 2 and 3, this obstruction is provided by means of a diffuser 36 which is formed on the lower surface of the flange 30 and has the cross-sectional shape of an air foil. As can be seen in FIG. 3, the largest cross-sectional thickness of the air foil diffuser element 36 is directly opposite the orifice 34 and then decreases in a tapering manner as it approaches the tips of the flange 30. Additionally as can be seen in FIG. 3, the width of the element 36 likewise decreases in a tapering manner as it approaches the tips of the flange 30. As can be easily appreciated, this arrangement compresses the air flow in the center opposite the orifice 34 and gradually releases it toward the tips achieving a uniform and laminar air flow across the mirror surface. As an example, the thickness of the air foil 36 may be such as to provide an effective air slit of 0.003 inches opposite the orifice 34 and 0.009 inches at the tips.

With the water and air dispensing nozzle arrangements described above, water supplied by the conduit 18 will, as a result of the capillary action between the flange 26 and the mirror surface and the shape of the flange 26, spread across the reflective surface 20 of the mirror in all directions and completely cover same. As a result of the laminar flow of the air exiting from the air dispensing nozzle 32 parallel to the surface of the mirror, the water will actually be siphoned or drawn across the surface of the mirror without turbulence.

It should be noted that in order to achieve this effect, within reasonable pressure limits, the spacing between the current of air and the underlying layer of water should be relatively small. In practice, thicknesses for the flange 26 in the order of 0.5mm have been found to be satisfactory.

In order to supply air and water to the mirror of FIG. 1 the free end of the handle 10 is threaded to receive a female connection of a flexible fluid conduit hose which for purposes of this invention likewise contains air and water conduits. The air and water conduits may if desired be provided with plug-in sockets (not shown) which plug into the handle 10, and are held in place when the female coupling is screwed onto the threaded end of the handle.

Figure 10:
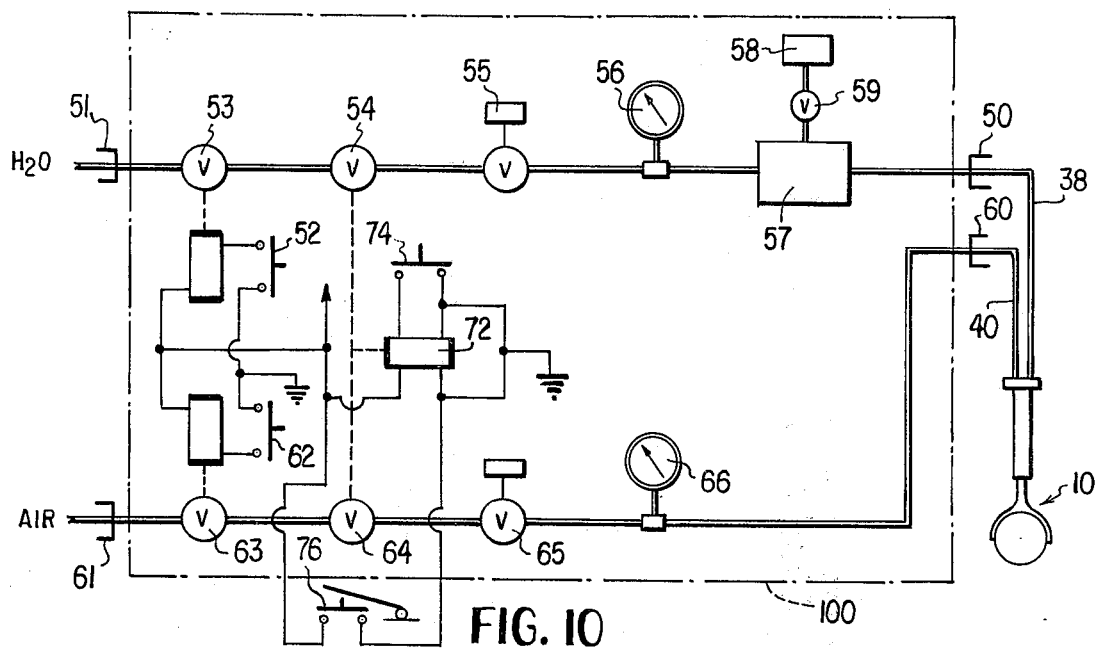
FIG. 10 is a schematic diagram of a preferred embodiment of a control system for the air and water streams for the self cleaning dental mirror according to the invention.

Referring now to FIG. 10 there is shown a schematic of the air and water controls for the self cleaning dental mirror according to the invention. The air and water controls for the self cleaning dental mirror are substantially all contained in a small compact unit indicated by the reference numeral 100 which can be easily mounted on the existing standard dentist console. As shown in FIG. 10, the flexible hose includes a water conduit 38 and a gas conduit 40 which are connected to a water conduit coupling 50 and an air conduit coupling 60 respectively, provided on the output side of the unit 100. Water and air are supplied to the unit 100 via couplings 51 and 61 respectively.

The water conduit coupling 51 is connected to a source of water under pressure, for example in the standard dentist's console. Contained in the unit 100 and connected in a water line between the couplings 51 and 50 are an on-off solenoid valve 53 controlled by an on-off switch 52, a master control solenoid valve 54 controlled by master control switch 74, a graduated metering control valve 55, a water pressure gauge 56, and a water reservoir mix bowl 57. Connected to the reservoir 57 via a surfactant bowl graduated one way metering control valve 59 is a replaceable bottle 58 of a surfactant concentrate. The one way valve 59 serves to meter controlled amounts of the surfactant, such as sodium deoxylbenzene sulfonate, etc., into the reservoir 57 where it mixes with the incoming water due to its natural siphoning flow interaction.

Air coupling 61 is connected to a high pressure air source, e.g., 0–80 psi found in the conventional dentist's console or to a pump system. Contained in the unit 100 and connected in an air line between the couplings 61 and 60 are an air control on-off solenoid valve 63 controlled by an air on-off switch 62, a master control air valve 64 which is coupled to the master control valve 54 in the water line for simultaneous operation and control of both fluids, a graduated metering air control valve 65 and an air pressure gauge 66.

Master control valves 54 and 64 are controlled by a common electrical solenoid 72 which when activated, simultaneously, either opens or closes both valves 54 and 64. The master switch 74 mounted on the control panel of unit 100 (FIG. 12) opens or closes the electric circuit to solenoid 72 for the simultaneous operation of valves 54 and 64. In order to permit simple control of the solenoid 72 by foot pedal action with or without simultaneous operation of the dentist's hi-speed drill a foot pedal switch 76 which is in parallel with the master control switch 74 is additionally provided in order to activate solenoid 72.

Figure 12:
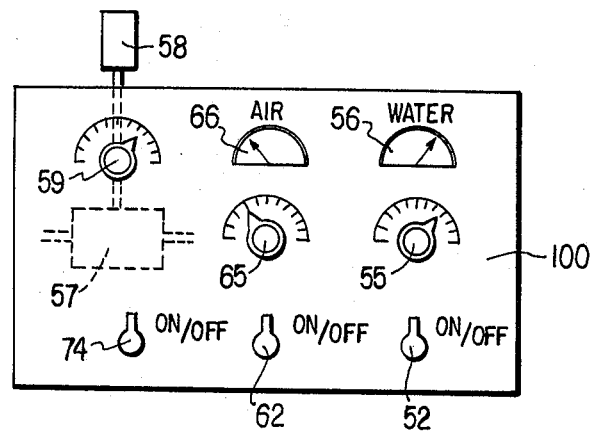
FIG. 12 is a front view of the console unit delivery system for the air and water control system.

FIG. 12 shows the control panel of the control console unit 100. FIG. 12 additionally shows the surfactant one way control valve 59, mounted in the console unit 100 to control the amount of surfactant metered into reservoir 57 from the surfactant concentrate bottle 58 which is preferably mounted above the unit 100. It is understood that the dental mirror according to the invention will work without any surfactant and that the use of a surfactant is a matter of choice.

In operation, one way valves 53 and 63 are opened by switches 52 and 62, and master control switch 74 is turned on, which in turn opens master control valves 54 and 64 by activating solenoid 72. The graduated water control valve 55 and air control valve 65 are adjusted to the proper operating pressures, e.g. 30 psi for the air flow and a pressure sufficient to produce two drops per second of water. The surfactant is adjusted to the desired metering control rate thereby mixing the surface tension reducer and water.

With the control valves in the open position as indicated above and with the water line connected to flexible conduit 38 via coupling 50 and the air line connected to flexible conduit 40 via coupling 60, water (mixed with surfactant if such is provided) under pressure is dispensed through orifice 29 into water dispensing nozzle 28. Because of the resulting capillary action due to the small opening of the water dispensing nozzle 28, water appears along the entire extent of the nozzle 28 and onto the reflective surface 20. The water tends to remain on the mirror surface 20 because of adhesion and/or surface tension reduction. Due to the shape of the water dispensing nozzle 28, the water covers the entire reflective surface 20. As air is dispensed from air dispensing nozzle 32 parallel to the surface 20 of the mirror 14 it blankets the water on the reflective surface spreading it thinly in a smooth laminar flow. It should be understood that the air pressure is greater than the water pressure, and that a moving frontal drop in air pressure exists below the air flow and above the water flow and therefore the air actually draws or siphons the water across the mirror 14. The water remains on the mirror surface and is not drawn up into the air flow, which would create a spray. As a result of the design of the air dispensing nozzle 32, air leaves the same with equal force along the entire extent thereof with relatively parallel vector force above and parallel to the mirror surface 20.

Figure 11:
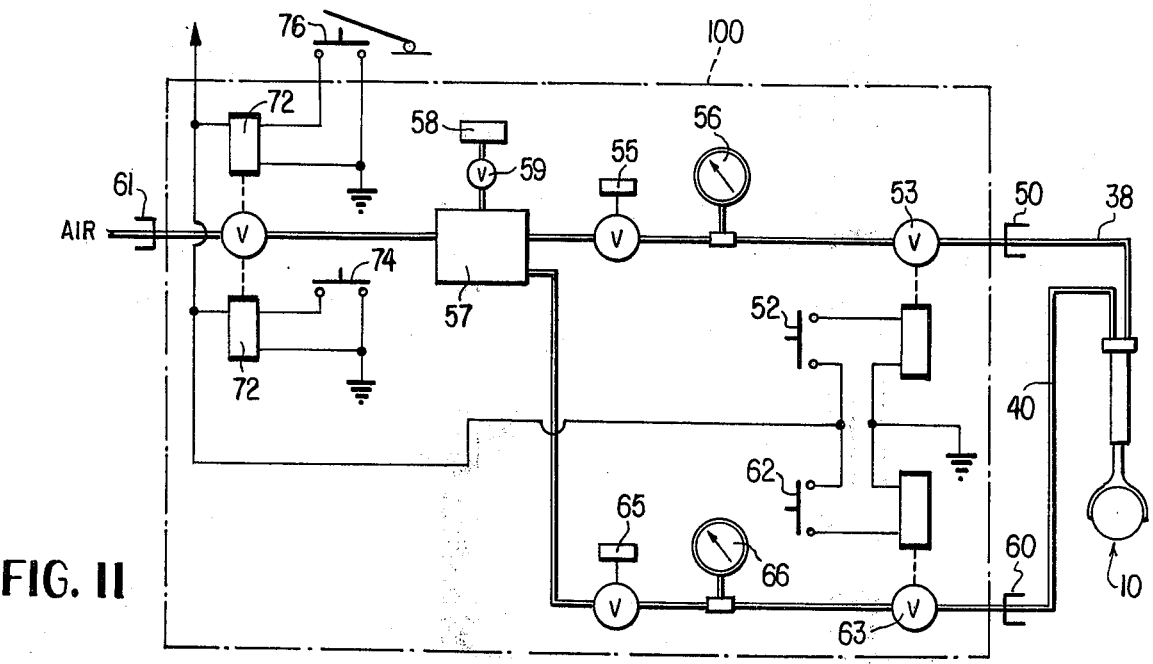
FIG. 11 is a schematic diagram of an alternative embodiment of an air and water control system.

FIG. 11 is a simplified air and water control system for the mirror of FIG. 1. According to this embodiment the water and the surfactant are manually mixed in the reservoir 57 and only a pressurized air source is required. In this arrangement the air line is connected to the reservoir and the air pressure is used to propel the liquid mixture through the system, thus eliminating a continuous water source and inlet line.

Although not illustrated it is anticipated that the dental mirror according to the invention could be equipped with a fiber optic lighting device by running fiber optic connecting rods to the mirror rim or to some other suitable place.

It should be noted that although the support 12 has been illustrated and described as being formed as a unitary structure, it is to be understood that the flanges 26 and 30 may be formed as separate pieces which are then fastened to the rim 24. Additionally it is to be understood that other arrangements for forming the diffuser 36 may be utilized, for example, by simply forming the underside of the flange 30 with a tapering surface which would allow the previously described frontal parallel, laminar air flow to emerge. Finally, it is to be understood that although the invention has been specifically described for use with a dental mirror, the principals of the invention are applicable to any self cleaning mirror surface.

It will be understood that the above description of the present invention is susceptible to various modifications, changes and adaptations, and the same are intended to be comprehended within the meaning and range of equivalents of the appended claims.

We claim:

1. In a dental mirror having a disk-like mirror, an elongated handle, and means at one end of said handle for supporting said mirror, the improvement comprising: a liquid conduit and a gas conduit extending through said handle; a first nozzle means disposed in said support means and extending along the periphery of said mirror, said first nozzle means being associated with said liquid conduit for dispensing a thin layer of a liquid onto the surface of said mirror, and a second nozzle means, disposed in said support means above said first nozzle means and associated with said gas conduit, for dispensing a thin layer of gas across and parallel to said surface of said mirror in a laminar flow above said layer of liquid to draw said layer of liquid across said surface of said mirror in a laminar flow.

2. A dental mirror as defined in claim 1 wherein said mirror is circular and wherein said support means and said first and second nozzle means extend along one half of the circumference of said mirror and are symmetrical with respect to said handle.

3. A dental mirror as defined in claim 2 wherein said support means includes a bottom plate having a portion thereof which is coplanar with said mirror and extends along said periphery, a top plate spaced from and above said portion of said bottom plate to form a hollow cavity therebetween and a flange positioned intermediate said top and bottom plates parallel to the surface of said mirror; said flange and said top plate being substantially identical in surface area, the space between said flange and said mirror surface and between said flange and said top plate constituting said first and second nozzle means respectively, and said flange being positioned above said surface of said mirror by a distance which is sufficiently small so that capillary action for the liquid results in said first nozzle means.

4. A dental mirror as defined in claim 3 wherein the effective opening of said second nozzle means increases gradually in a direction from said handle toward said tips to produce a uniform equalized laminar flow of gas along the entire extent of said first nozzle means.

5. A dental mirror as defined in claim 4 wherein a stationary air vane is formed on one of the surfaces defining said second nozzle means to cause said increase in the effective opening of said second nozzle means.

6. A dental mirror as defined in claim 5 wherein said stationary air vane has an air foil shape with the largest cross sectional thickness opposite said handle and a gradually decreasing thickness as it approaches the tips of said flange and top plate.

7. A dental mirror as defined in claim 5 wherein said air vane is formed on the lower surface of said top plate.

8. A dental mirror as defined in claim 3 wherein said top plate and said flange narrowingly taper in width in a direction from said handle toward the tips thereof.

9. A dental mirror as defined in claim 1, wherein said liquid is water and said gas is air.

10. A dental mirror as defined in claim 9, wherein said liquid is mixed with a surfactant.

11. A dental mirror as defined in claim 1, further comprising a first pressure control means for supplying liquid under pressure to said liquid conduit and a second pressure control means for supplying gas to said gas conduit at a greater pressure than that of said liquid.

12. A dental mirror as defined in claim 11, further comprising means for metering a desired quantity of a surfactant into said liquid, whereby said liquid and surfactant are dispensed at a lesser pressure than said gas.

13. A self cleaning mirror apparatus comprising in combination: a mirror surface; a first nozzle means disposed along one edge of said mirror surface for dispensing a thin layer of a liquid onto said surface; a second nozzle means disposed immediately above said first nozzle means and coextenxive therewith for dispensing a thin laminar layer of gas across and parallel to said mirror surface at a pressure greater than that of said layer of liquid to draw said layer of liquid across said mirror surface in a laminar flow; and means for simultaneously supplying liquid under pressure and gas under pressure to said first and second nozzle means, respectively.

14. A self cleaning dental mirror as defined in claim 1 further comprising means for simultaneously supplying liquid under pressure to said first nozzle means via said liquid conduit and gas under pressure to said second nozzle means via said gas conduit.

15. A self cleaning dental mirror as defined in claim 1 wherein: said support means and said first and second nozzle means are symmetrical with respect to said handle; and said support means includes: a bottom plate having a portion whose upper surface is coplanar with said surface of said mirror and extends along said periphery, a top plate spaced from and above said portion of said bottom plate to form a hollow cavity therebetween and a flange positioned intermediate said top and bottom plates parallel to said surface of said mirror; said flange and said top plate being substantially identical in surface area, the space between said flange and said mirror surface and between said flange and said top plate constituting said first and second nozzle means respectively, and said flange being positioned above said surface of said mirror by a distance which is sufficiently small so that capillary action for the liquid results in said first nozzle means.

16. A self cleaning mirror apparatus comprising in combination: a mirror surface; a first means disposed along one edge of said mirror surface for dispensing a thin layer of a liquid onto said surface; and a second means disposed immediately above said first means and coextensive therewith for simultaneously dispensing a thin laminar layer of gas across and parallel to said mirror surface at a pressure greater than that of said layer of liquid.

* * * * *